(12) United States Patent
Trim et al.

(10) Patent No.: US 11,740,218 B2
(45) Date of Patent: Aug. 29, 2023

(54) SYSTEM AND METHOD FOR PREDICTIVELY SENSING HARMFUL ENVIRONMENTAL CONDITIONS BASED ON LOCATION AND HISTORICAL USER DATA

(71) Applicant: DELL PRODUCTS, LP, Round Rock, TX (US)

(72) Inventors: James D. Trim, Pflugerville, TX (US); Jace W. Files, Round Rock, TX (US); John T. Morrison, Round Rock, TX (US); Sajjad Ahmed, Austin, TX (US)

(73) Assignee: Dell Products L.P., Round Rock, TX (US)

( * ) Notice: Subject to any disclaimer, the term of this patent is extended or adjusted under 35 U.S.C. 154(b) by 326 days.

(21) Appl. No.: 17/142,588

(22) Filed: Jan. 6, 2021

(65) Prior Publication Data
US 2022/0214324 A1 Jul. 7, 2022

(51) Int. Cl.
*G06F 16/245* (2019.01)
*G06F 16/29* (2019.01)
*G01N 33/00* (2006.01)
*G05B 15/02* (2006.01)
*G06N 5/04* (2023.01)

(52) U.S. Cl.
CPC ......... *G01N 33/0063* (2013.01); *G05B 15/02* (2013.01); *G06F 16/245* (2019.01); *G06F 16/29* (2019.01); *G06N 5/04* (2013.01); *G01N 33/004* (2013.01); *G01N 33/0047* (2013.01); *G01N 2033/0068* (2013.01)

(58) Field of Classification Search
CPC ....... G01N 33/0063; G01N 2033/0068; G01N 33/004; G01N 33/0047; G01N 33/0075; G01N 33/0073; G01N 33/0036; G01N 33/0004; G05B 21/02; G05B 15/02; G05B 13/028; G06F 16/245; G06F 16/29; G06F 17/18; G06F 1/32; G06F 1/3203; G06F 16/24575; G06N 5/04; G06N 3/02; G06N 20/00
USPC ............... 340/3.1, 539.22–539.29, 540, 601; 700/13–19; 702/2–3, 24, 32, 140, 150, 702/187–189
See application file for complete search history.

(56) References Cited

U.S. PATENT DOCUMENTS

| 8,204,786 | B2 * | 6/2012 | LeBoeuf | A61B 5/14546 600/595 |
| 11,086,308 | B2 * | 8/2021 | Chen | G05B 23/0221 |
| 2016/0125307 | A1 * | 5/2016 | Zheng | G06N 3/08 706/20 |
| 2017/0067747 | A1 * | 3/2017 | Ricci | G08B 25/016 |

(Continued)

FOREIGN PATENT DOCUMENTS

CN 107085070 A * 8/2017 ......... G01N 33/0004

*Primary Examiner* — Jeffrey P Aiello
(74) *Attorney, Agent, or Firm* — Larson Newman, LLP (57) ABSTRACT

A sensor measures an environmental factor in an ambient environment immediately surrounding an information handling system. A processor determines that the information handling system is in a first location, provides a first sampling frequency of the sensor based upon the first location, determines that the information handling system is in a second location, and provides a second sampling frequency of the sensor based upon the second location. The first sampling frequency is different from the second sampling frequency.

18 Claims, 4 Drawing Sheets

(56) References Cited

U.S. PATENT DOCUMENTS

2018/0073951 A1* 3/2018 Venkatraman ........ H04W 4/023
2018/0216990 A1* 8/2018 Rothwell .................. G01H 1/00
2019/0069245 A1* 2/2019 Miller .................. A61B 5/7221
2020/0190775 A1* 6/2020 Selvaraj .................. E02F 9/261

* cited by examiner

SYSTEM AND METHOD FOR PREDICTIVELY SENSING HARMFUL ENVIRONMENTAL CONDITIONS BASED ON LOCATION AND HISTORICAL USER DATA

FIELD OF THE DISCLOSURE

This disclosure generally relates to information handling systems, and more particularly relates to predictively sensing harmful environmental conditions based on geographic location and historical user data.

As the value and use of information continues to increase, individuals and businesses seek additional ways to process and store information. One option is an information handling system. An information handling system generally processes, compiles, stores, and/or communicates information or data for business, personal, or other purposes. Because technology and information handling needs and requirements may vary between different applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, reservations, enterprise data storage, or global communications. In addition, information handling systems may include a variety of hardware and software resources that may be configured to process, store, and communicate information and may include one or more computer systems, data storage systems, and networking systems.

SUMMARY

An information handling system may include a sensor and a processor. The sensor may measure an environmental factor in an ambient environment immediately surrounding the information handling system. The processor may determine that the information handling system is in a first location, provide a first sampling frequency of the sensor based upon the first location, determine that the information handling system is in a second location, and provide a second sampling frequency of the sensor based upon the second location. The first sampling frequency may be different from the second sampling frequency

BRIEF DESCRIPTION OF THE DRAWINGS

It will be appreciated that for simplicity and clarity of illustration, elements illustrated in the Figures have not necessarily been drawn to scale. For example, the dimensions of some of the elements are exaggerated relative to other elements. Embodiments incorporating teachings of the present disclosure are shown and described with respect to the drawings presented herein, in which.

The use of the same reference symbols in different drawings indicates similar or identical items.

DETAILED DESCRIPTION OF DRAWINGS

The following description in combination with the Figures is provided to assist in understanding the teachings disclosed herein. The following discussion will focus on specific implementations and embodiments of the teachings. This focus is provided to assist in describing the teachings, and should not be interpreted as a limitation on the scope or applicability of the teachings. However, other teachings can certainly be used in this application. The teachings can also be used in other applications, and with several different types of architectures, such as distributed computing architectures, client/server architectures, or middleware server architectures and associated resources.

Figure 1:
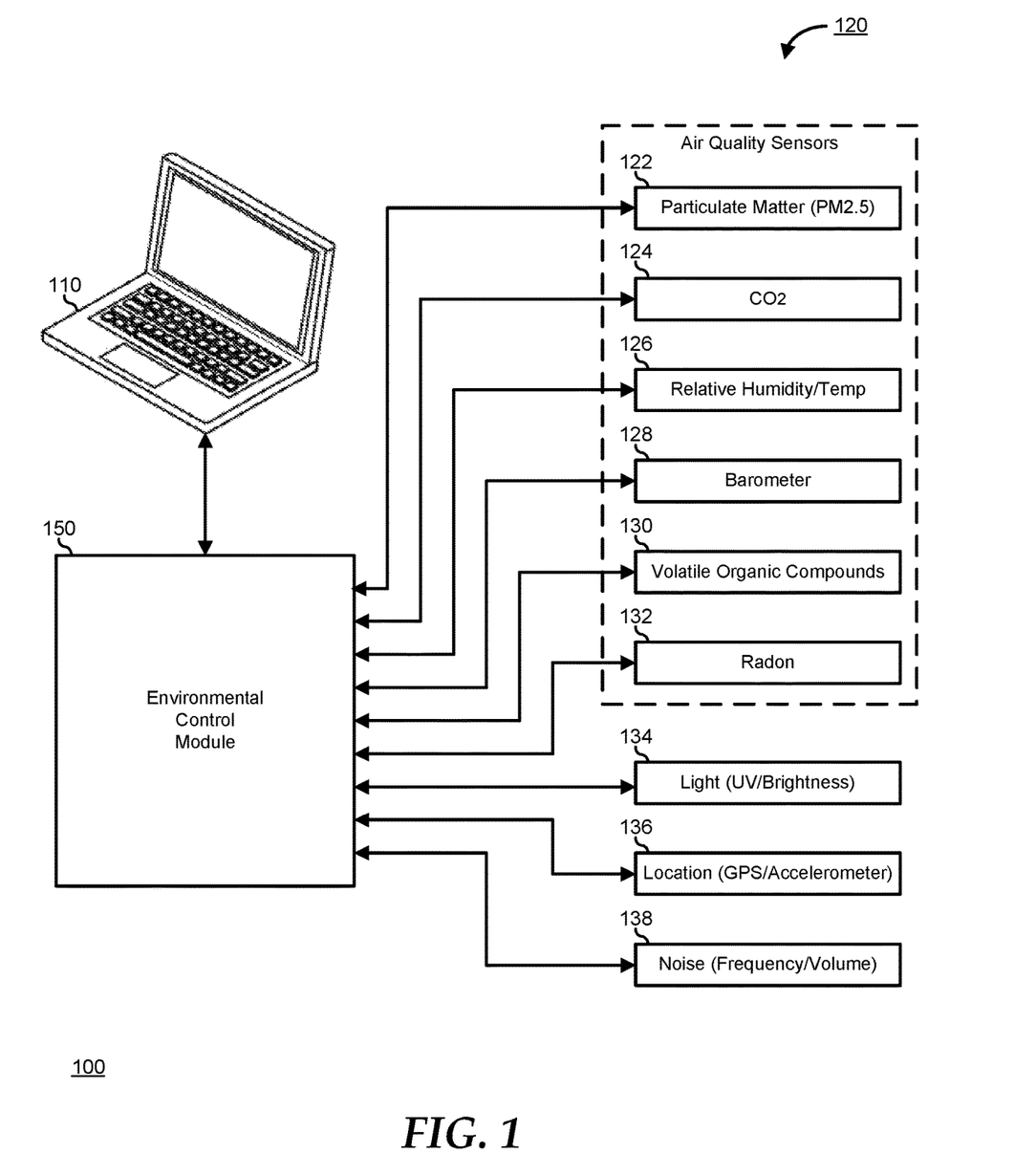
FIG. 1 is a block diagram illustrating an information handling system according to an embodiment of the current disclosure.

FIG. 1 illustrates a green processing system 100. Green processing system 100 represents an element of processing equipment that is designed and manufactured in accordance with various environmental sustainability goals, such as increased use of recycled and recyclable materials or materials that otherwise carry a lower carbon footprint in their manufacture, lower power consumption technologies, more healthy processing environments for the users of the processing equipment, and the like. In a particular embodiment, green processing system 100 is configured to monitor the processing environment in which the green processing system is utilized, or is projected to be utilized through the inclusion of various environmental sensors, and to dynamically adjust the data acquisition rates for environmental sensors to optimize the balance of keeping a user aware when in a higher potentially harmful environment and, when needed, to lower the rate of data acquisition by the environmental sensors, thereby reducing system resource load, lowering overall energy usage, and improving battery usage.

Green processing system 100 includes an information handling system 110 that includes environmental sensors 120 and an environmental control module 150. Information handling system 110 represents a wide variety of types of computer systems, as needed or desired. As illustrated, information handling system 110 represents a laptop computer system, but the information handling system may be understood more broadly to represent other consumer oriented computer systems, such as tablet devices, cellular devices, smart phone, home desktop systems, other consumer oriented computer systems, as needed or desired. Moreover, information handling system 110 may be understood to represent a wide variety of types of commercial computer systems, such as slim client systems, workstations, office server systems, or other commercial computer systems, as needed or desired. Further, in its capacity to monitor and manage power consumption or processing resources, as described below, the teachings of the current disclosure may further be applied to datacenter equipment, such as server systems, blade- or sled-based processing systems, storage racks, I/O racks, switching racks, or other datacenter equipment, as needed or desired.

Environmental sensors 120 include various air quality sensors including a particulate matter sensor 122, a $CO_2$ sensor 124, a relative humidity/temperature sensor 126, a barometric pressure sensor 128, a volatile organic compound (VOC) sensor 130, and a radon sensor 132. Particulate matter sensor 122 represents a sensor that detects the presence of fine particulate matter in the ambient air around green processing system 100. Fine particulate matter may include soot, dust, smoke, dirt, pollen, and the like. Fine particulate matter is typically measured in micrometers, and current environmental standards are concerned with fine particulate matter that is less than 2.5 micrometers in diameter. Hence a common particulate matter sensor may be designated as a PM2.5 sensor. $CO_2$ sensor 124 detects the amount of $CO_2$ in the ambient air around green processing system 100. Various studies have shown that decision making and productivity issues may occur when $CO_2$ levels are greater than 1000 parts per million (ppm), and severe problems may occur at levels greater than 2500 ppm. It has been further understood that air recirculation in buildings may contribute to higher $CO_2$ levels. Relative humidity/temperature sensor 126 and barometric pressure sensor 128 represent sensors to detect atmospheric conditions, either as a function of the weather in the area of green processing system 100, or as a result of the environmental conditioning in the vicinity of the green processing system. In either case, the atmospheric conditions surrounding green processing system 100 may have impacts on user health, productivity, sense of well-being, or the like. VOC sensor 128 represents a sensor that detects airborne chemicals or toxins that may have impacts on user health, productivity, sense of well-being, or the like. VOCs may include acetone, acetic acid, butanal, carbon disulfide, ethanol, alcohol, formaldehyde, methylene chloride, sulfur, or other compounds and may, in some cases, be considered as carcinogenic. VOCs may be present in the ambient air surrounding green processing system 100, or may be outgassed from materials in the vicinity of the green processing system. Radon sensor 130 represents a sensor to detect radon in the ambient air surrounding green processing system 100. Radon is a naturally occurring radioactive element that outgasses from the earth's surface, at rates which may vary due to the underlying geological strata at the particular location. However the concentration of radon in the ambient air surrounding green processing system 100 may be increased beyond the naturally occurring concentration due to poor ventilation or other environmental factors.

Other environmental sensors 120 include a light sensor 134, a location sensor 136, and a noise sensor 138. Light sensor 134 represents a photodetector that operates to detect light in the ambient environment of green processing system 100, and can include detectors for detecting the spectrum of the ambient light, including in the ultraviolet (UV) range, and can detect the brightness of the ambient light. Location sensor 136 represents various positional sensors of green processing system 100, including a global positioning system (GPS), a wide area network (WAN) locator system, an accelerometer or other motion detector whereby the green processing system can determine relative location with respect to a fixed location determined by the GPS or WAN locator system, or other sensors configured to determine the location of the green processing system. Noise sensor 138 represents a microphone or other sound receiving sensor that can determine a frequency spectrum of the received sound in the ambient environment of green processing system 100, the volume of the received sound, or the like.

It will be understood that each of sensors 120 may consume power within green processing system 100, based upon the receipt and analysis of the various environmental factors measured by the various sensors. For example, while operating, particulate matter sensor 122 and $CO_2$ sensor 124 may consume on the order of 600 milliwatts (mW) of power. Other sensors 120 may similarly consume power within green processing system 100. As such, operating all of sensors 120 simultaneously may result in an undue burden on the power resources of green processing system 100, such as a battery or the like. Thus, it may be desirable to determine a sampling frequency for each of sensors 120, based upon the type of ambient condition that is being measured, and the rate at which such conditions are likely to change. Moreover, each of sensors 120 may be understood to necessitate the consumption of system resources of information handling system 110, such as processor cycles, memory resources, memory and I/O bandwidth, and the like. In particular, each one of sensors 120 may be associated with its own driver or other application programming interface (API) that utilizes processing resources to run. Thus, as with the power consumption described above, it may be desirable to minimize the amount of sampling done by each of sensors 120 in order to reduce the processing load on information handling system 110.

Sensors 120 are each connected to environmental control module 150. Here, environmental control module 150 may be understood to represent hardware needed to interface with one or more of sensors 120, software, such as drivers and APIs needed to operate the sensors, or a combination thereof. In addition, environmental control module 150 operates to manage the sampling frequencies of sensors 120, the power consumed by the sensors, the processing resources consumed by the sensors, and the like. As described further below, environmental control module 150 further operates to leverage historical data from sensors 120, user location and location history data, external data resources, and the like, to modify the sampling frequencies, the power consumption, and the processing resource consumption of sensors 120 in order to intelligently optimize the performance of the sensors and of information handling system 110, and to improve the health and wellbeing of the user of green processing system 100.

Figure 2:
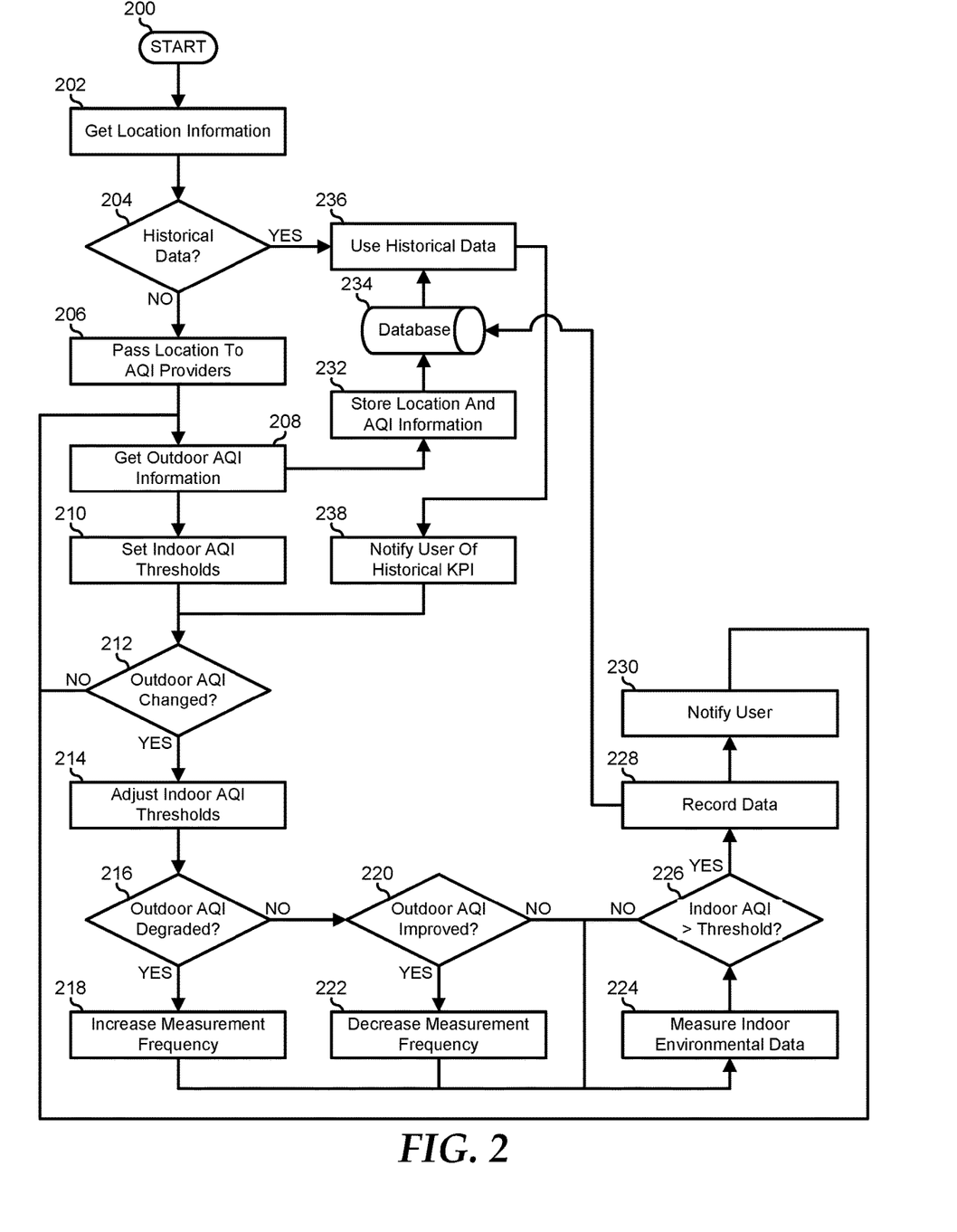
FIG. 2 is a flowchart illustrating a method for the dynamic adjustment of thresholds for sampling frequencies of sensors in an information handling system.
Figure 3:
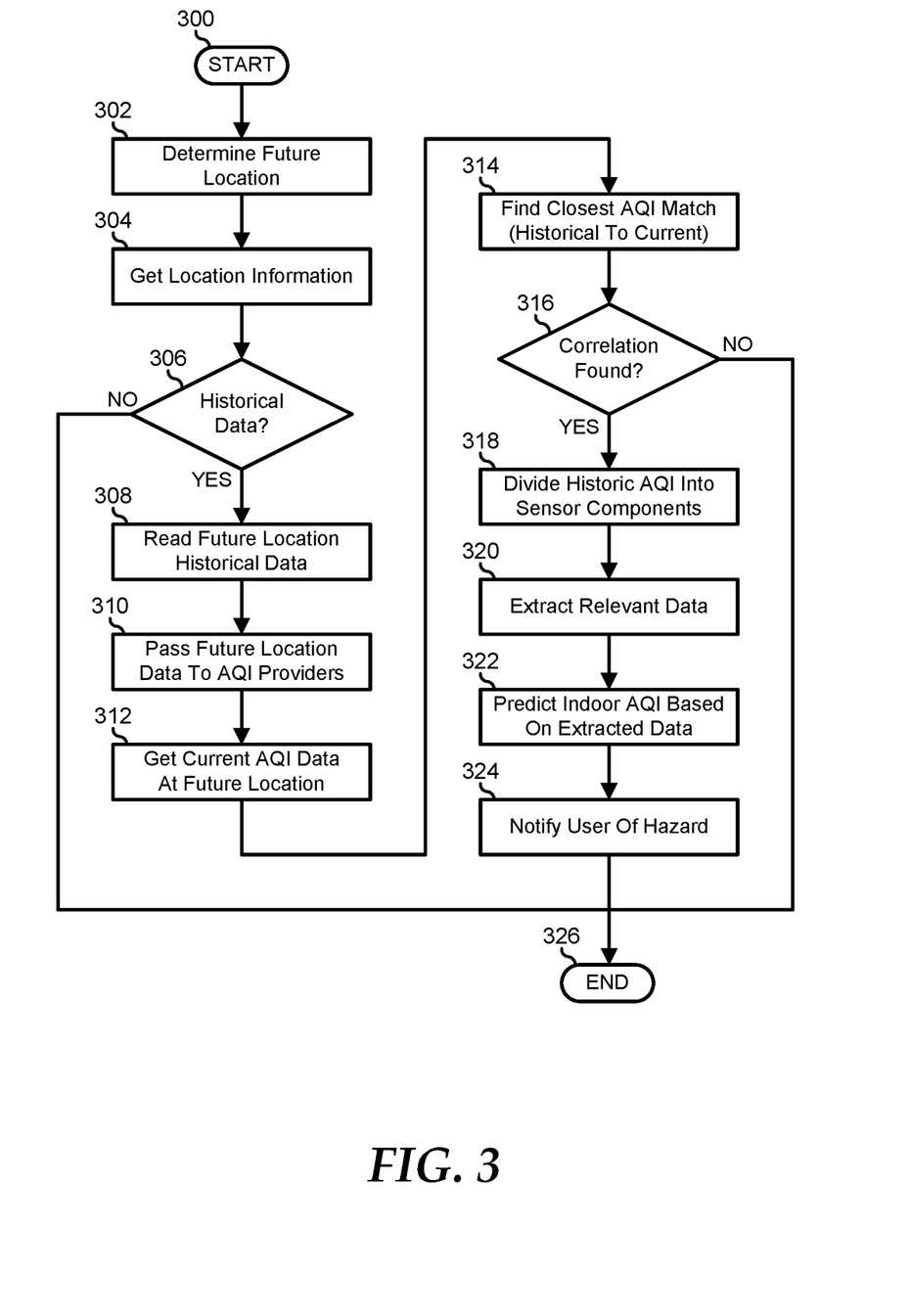
FIG. 3 is a flowchart illustrating a method of predicting environmental conditions to modify acquisition rates of the sensors of an information handling system.

The functions and features of green processing system 110, and particularly of environmental control module 150 will be illustrated hereafter with reference to FIGS. 2 and 3, which provide flowcharts illustrating the functions and features of the green processing system. Note that the AQI indicators may be represented as a single number that aggregates the air quality as to a number of different environmental factors. For example, an AQI may be utilized that is an aggregation of particulate matter index, a CO2 index, a VOC index, or other separate indexes, as needed or desired. On the other hand, the AQI indicators may also be understood to represent each of the individual indexes. In this regard, as describe below, the actions taken can be based upon an aggregate AQI indication, upon separate AQI indications, or on a combination thereof. For example, where a user has a particular known susceptibility to particulate matter, the methods below can be understood in terms of a first flow for the aggregate AQI indication, and a second flow for the particulate matter index, and warnings and actions for the sensors related to the aggregate AQI indication can be taken separately, or in conjunction with the warnings and actions for the particulate matter sensor and the related particulate matter indication, as needed or desired.

FIG. 2 illustrates a method for the dynamic adjustment of thresholds for sampling frequencies of sensors in an information handling system utilizing indoor and outdoor air quality index (AQI) indicators based upon the context or location of the information handling system. The method starts at block 200. Location information for the information handling system is gathered in block 202. For example, one or more location sensor can determine the current location of an information handling system. A decision is made as to whether or not historical AQI information is available for the location in decision block 204. If not, the "NO" branch of decision block 204 is taken and the method proceeds to block 206, as described below. If historical AQI information is available, the "YES" branch of decision block 204 is taken, the historical the AQI information is utilized in block 236, the user of the information handling system is notified of the key performance indicator (KPI) associated with the historical AQI information in block 238, and the method proceeds to decision block 212, as described below. Note here that, when the historical AQI information is used in block 236, the historical AQI information is retrieved from a historical AQI database 234 that provides indexed AQI information for aggregated AQI indications and separate AQI indications, as needed or desired. Databases are known in the art, and the functions and features of the historical AQI database 234 will not be further described herein, except as needed to illustrate the current embodiments.

Returning to decision block 204, when historical AQI information is not available, and the "NO" branch is taken, the location information from block 202 is passed to various AQI information providers in block 206. Here, for example, a web interface of the information handling system may be invoked to gather the various AQI information from public or private sources of such information. Thus, where public AQI information is published in a location addressable form, the web interface can provide the location information to the public AQI information website to retrieve the AQI information for that location. On the other hand, where private AQI information is available, for example, on a subscription basis, the web interface can provide the location information to the private AQI information website, along with credential information to access the private AQI information, as needed or desired.

In either case, the AQI information providers return the associated AQI information for the location in block 208. Here, in a first branch, the location information and the AQI information is stored in block 232 to historical AQI database 234 for future use. For example, at a future time, when the information handling system as returned to the particular location, the "YES" branch of decision block 204 can be taken and the AQI information can be retrieved from historical QAI database 234 for use in block 236. In a second branch, the received AQI information is utilized to set one or more AQI threshold for the information handling system in block 210. Here, for example, if a particular AQI indication is known to be particularly high or particularly low in a given location, a threshold for that AQI indication can be set at a level higher than the known level. In this way, any alerts generated are provided within the context of the known level for that AQI indication.

After the AQI thresholds are set in block 210, or after the user of the information handling system is notified of the KPI associated with the historical AQI information in block 238, a decision is made as to whether the AQI information has changed in decision block 212. If not, the "NO" branch of decision block 212 is taken and the method returns to block 208 where the AQI information is retrieved for the location. If the AQI information has changed, the "YES" branch of decision block 212 is taken and the AQI thresholds are adjusted in block 214, and a decision is made as to whether or not the AQI information has degraded in decision block 216. If so, the "YES" branch of decision block 216 is taken, the measurement frequency for the associated sensors is increased in block 218, and the AQI information for is measured by the information handling system in block 224. If the AQI information has not degraded, the "NO" branch of decision block 216 is taken and a decision is made as to whether or not the AQI information has improved in decision block 220. If so, the "YES" branch of decision block 220 is taken, the measurement frequency for the associated sensors is decreased in block 222, and the AQI information for is measured by the information handling system in block 224. If the AQI information has not improved, that is, when the AQI information as remained constant, the "NO" branch of decision block 220 is taken and AQI information for is measured by the information handling system in block 224.

A decision is made as to whether or not the AQI as measured by the information handling system is greater than a threshold for that particular AQI in decision block 226. If not, the "NO" branch of decision block 226 is taken and the method returns to block 224 where the AQI information for is measured by the information handling system. If the AQI as measured by the information handling system is greater than the threshold for the particular AQI, the "YES" branch of decision block 226 is taken, the AQI as measured by the information handling system is recorded to historical AQI database 234 in block 228, the user is notified that the AQI as measured by the information handling system is greater than a threshold for that particular AQI in block 230, and the method returns to block 208 where, the AQI information providers return the associated AQI information for the location of the information handling system.

FIG. 3 illustrates a method of predicting environmental conditions, such as the various AQI indications, in order to modify acquisition rates of the sensors of an information handling system based on historical AQI information. The method begins at block 300. A future location of an information handling system is determined in block 302. For example, a user may take a laptop computer system from a home location to a work location on a daily basis. Here, when the laptop computer system is presently at the home location, it can be determined that the future location will be the work location. Location information for the future location of the information handling system is gathered in block 304. A decision is made as to whether or not historical AQI information for the future location is available in decision block 306. If not, the "NO" branch of decision block 306 is taken and the method ends in block 326. If historical AQI information for the future location is available, the "YES" branch of decision block 306 is taken, and the historical AQI information for the future location is read from a historical AQI database in block 308. The future location information from block 302 is passed to various AQI information providers in block 310, and the current AQI information from at the future location is received in block 312.

A closest match between the historical AQI information for the future location and the current AQI information at the future location is compared to fine a closest match in block 314, and a decision is made as to whether or not a correlation between the historical AQI information for the future location and the current AQI information at the future location is found in decision block 316. If not, the "NO" branch of decision block 316 is taken and the method ends in block 326. If a correlation between the historical AQI information for the future location and the current AQI information at the future location is found, the "YES" branch of decision block 316 is taken and the historical AQI information is divided into the associated component sensor data in block 318. The relevant data from the historical AQI information is extracted in block 320, and an expected AQI for the future location is predicted based upon the extracted information in block 322. The user of the information handling system is notified of the predicted AQI for the future location in block 324, and the method ends in block 326.

Figure 4:
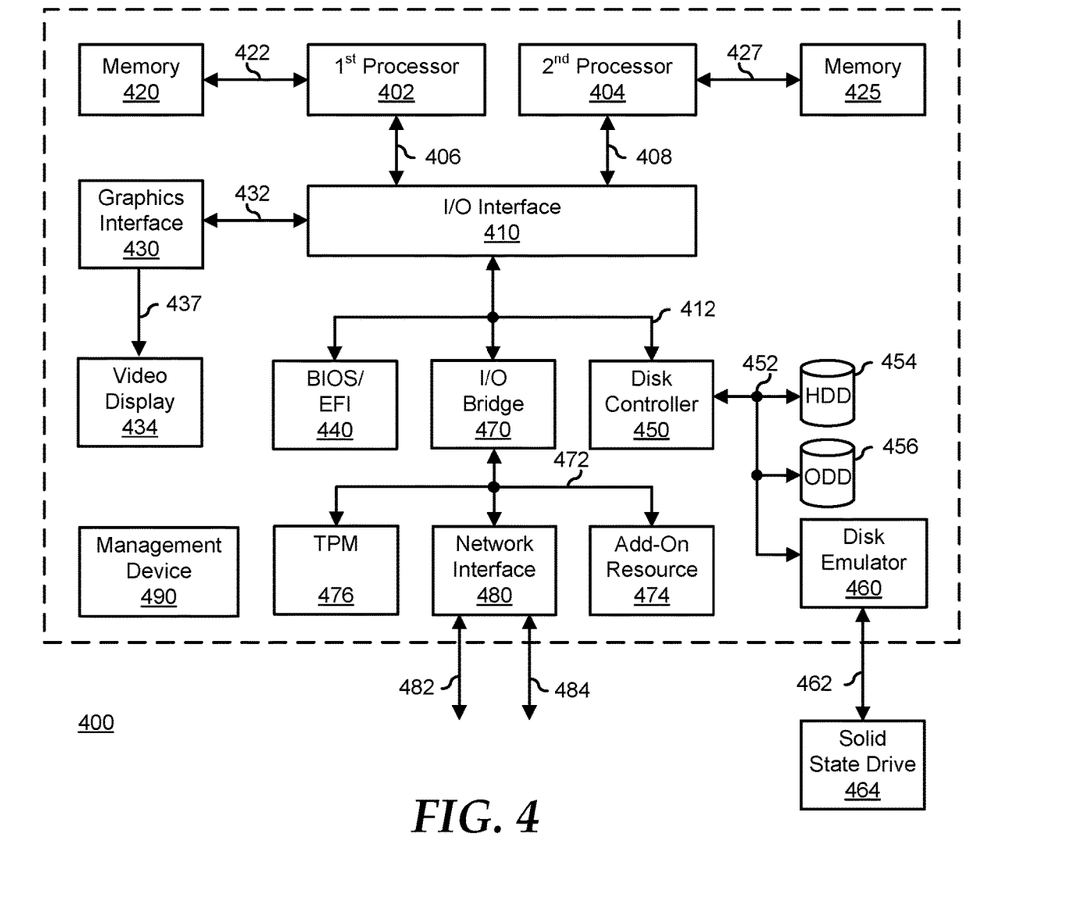
FIG. 4 is a block diagram illustrating a generalized information handling system according to another embodiment of the present disclosure.

FIG. 4 illustrates a generalized embodiment of an information handling system 400. For purpose of this disclosure an information handling system can include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, entertainment, or other purposes. For example, information handling system 400 can be a personal computer, a laptop computer, a smart phone, a tablet device or other consumer electronic device, a network server, a network storage device, a switch router or other network communication device, or any other suitable device and may vary in size, shape, performance, functionality, and price. Further, information handling system 400 can include processing resources for executing machine-executable code, such as a central processing unit (CPU), a programmable logic array (PLA), an embedded device such as a System-on-a-Chip (SoC), or other control logic hardware. Information handling system 400 can also include one or more computer-readable medium for storing machine-executable code, such as software or data. Additional components of information handling system 400 can include one or more storage devices that can store machine-executable code, one or more communications ports for communicating with external devices, and various input and output (I/O) devices, such as a keyboard, a mouse, and a video display. Information handling system 400 can also include one or more buses operable to transmit information between the various hardware components.

Information handling system 400 can include devices or modules that embody one or more of the devices or modules described below, and operates to perform one or more of the methods described below. Information handling system 400 includes a processors 402 and 404, an input/output (I/O) interface 410, memories 420 and 425, a graphics interface 430, a basic input and output system/universal extensible firmware interface (BIOS/UEFI) module 440, a disk controller 450, a hard disk drive (HDD) 454, an optical disk drive (ODD) 456, a disk emulator 460 connected to an external solid state drive (SSD) 462, an I/O bridge 470, one or more add-on resources 474, a trusted platform module (TPM) 476, a network interface 480, a management device 490, and a power supply 495. Processors 402 and 404, I/O interface 410, memory 420, graphics interface 430, BIOS/UEFI module 440, disk controller 450, HDD 454, ODD 456, disk emulator 460, SSD 462, I/O bridge 470, add-on resources 474, TPM 476, and network interface 480 operate together to provide a host environment of information handling system 400 that operates to provide the data processing functionality of the information handling system. The host environment operates to execute machine-executable code, including platform BIOS/UEFI code, device firmware, operating system code, applications, programs, and the like, to perform the data processing tasks associated with information handling system 400.

In the host environment, processor 402 is connected to I/O interface 410 via processor interface 406, and processor 404 is connected to the I/O interface via processor interface 408. Memory 420 is connected to processor 402 via a memory interface 422. Memory 425 is connected to processor 404 via a memory interface 427. Graphics interface 430 is connected to I/O interface 410 via a graphics interface 432, and provides a video display output 436 to a video display 434. In a particular embodiment, information handling system 400 includes separate memories that are dedicated to each of processors 402 and 404 via separate memory interfaces. An example of memories 420 and 430 include random access memory (RAM) such as static RAM (SRAM), dynamic RAM (DRAM), non-volatile RAM (NV-RAM), or the like, read only memory (ROM), another type of memory, or a combination thereof.

BIOS/UEFI module 440, disk controller 450, and I/O bridge 470 are connected to I/O interface 410 via an I/O channel 412. An example of I/O channel 412 includes a Peripheral Component Interconnect (PCI) interface, a PCI-Extended (PCI-X) interface, a high-speed PCI-Express (PCIe) interface, another industry standard or proprietary communication interface, or a combination thereof. I/O interface 410 can also include one or more other I/O interfaces, including an Industry Standard Architecture (ISA) interface, a Small Computer Serial Interface (SCSI) interface, an Inter-Integrated Circuit ($I^2C$) interface, a System Packet Interface (SPI), a Universal Serial Bus (USB), another interface, or a combination thereof. BIOS/UEFI module 440 includes BIOS/UEFI code operable to detect resources within information handling system 400, to provide drivers for the resources, initialize the resources, and access the resources. BIOS/UEFI module 440 includes code that operates to detect resources within information handling system 400, to provide drivers for the resources, to initialize the resources, and to access the resources.

Disk controller 450 includes a disk interface 452 that connects the disk controller to HDD 454, to ODD 456, and to disk emulator 460. An example of disk interface 452 includes an Integrated Drive Electronics (IDE) interface, an Advanced Technology Attachment (ATA) such as a parallel ATA (PATA) interface or a serial ATA (SATA) interface, a SCSI interface, a USB interface, a proprietary interface, or a combination thereof. Disk emulator 460 permits SSD 464 to be connected to information handling system 400 via an external interface 462. An example of external interface 462 includes a USB interface, an IEEE 1394 (Firewire) interface, a proprietary interface, or a combination thereof. Alternatively, solid-state drive 464 can be disposed within information handling system 400.

I/O bridge 470 includes a peripheral interface 472 that connects the I/O bridge to add-on resource 474, to TPM 476, and to network interface 480. Peripheral interface 472 can be the same type of interface as I/O channel 412, or can be a different type of interface. As such, I/O bridge 470 extends the capacity of I/O channel 412 when peripheral interface 472 and the I/O channel are of the same type, and the I/O bridge translates information from a format suitable to the I/O channel to a format suitable to the peripheral channel 472 when they are of a different type. Add-on resource 474 can include a data storage system, an additional graphics interface, a network interface card (NIC), a sound/video processing card, another add-on resource, or a combination thereof. Add-on resource 474 can be on a main circuit board, on separate circuit board or add-in card disposed within information handling system 400, a device that is external to the information handling system, or a combination thereof.

Network interface 480 represents a NIC disposed within information handling system 400, on a main circuit board of the information handling system, integrated onto another component such as I/O interface 410, in another suitable location, or a combination thereof. Network interface device 480 includes network channels 482 and 484 that provide interfaces to devices that are external to information handling system 400. In a particular embodiment, network channels 482 and 484 are of a different type than peripheral channel 472 and network interface 480 translates information from a format suitable to the peripheral channel to a format suitable to external devices. An example of network channels 482 and 484 includes InfiniBand channels, Fibre Channel channels, Gigabit Ethernet channels, proprietary channel architectures, or a combination thereof. Network channels 482 and 484 can be connected to external network resources (not illustrated). The network resource can include another information handling system, a data storage system, another network, a grid management system, another suitable resource, or a combination thereof.

Management device 490 represents one or more processing devices, such as a dedicated baseboard management controller (BMC) System-on-a-Chip (SoC) device, one or more associated memory devices, one or more network interface devices, a complex programmable logic device (CPLD), and the like, that operate together to provide the management environment for information handling system 400. In particular, management device 490 is connected to various components of the host environment via various internal communication interfaces, such as a Low Pin Count (LPC) interface, an Inter-Integrated-Circuit (I2C) interface, a PCIe interface, or the like, to provide an out-of-band (OOB) mechanism to retrieve information related to the operation of the host environment, to provide BIOS/UEFI or system firmware updates, to manage non-processing components of information handling system 400, such as system cooling fans and power supplies. Management device 490 can include a network connection to an external management system, and the management device can communicate with the management system to report status information for information handling system 400, to receive BIOS/UEFI or system firmware updates, or to perform other task for managing and controlling the operation of information handling system 400. Management device 490 can operate off of a separate power plane from the components of the host environment so that the management device receives power to manage information handling system 400 when the information handling system is otherwise shut down. An example of management device 490 include a commercially available BMC product or other device that operates in accordance with an Intelligent Platform Management Initiative (IPMI) specification, a Web Services Management (WSMan) interface, a Redfish Application Programming Interface (API), another Distributed Management Task Force (DMTF), or other management standard, and can include an Integrated Dell Remote Access Controller (iDRAC), an Embedded Controller (EC), or the like. Management device 490 may further include associated memory devices, logic devices, security devices, or the like, as needed or desired.

Although only a few exemplary embodiments have been described in detail herein, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

The above-disclosed subject matter is to be considered illustrative, and not restrictive, and the appended claims are intended to cover any and all such modifications, enhancements, and other embodiments that fall within the scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An information handling system, comprising:
   a sensor configured to measure an environmental factor in an ambient environment immediately surrounding the information handling system;
   a processor configured to determine that the information handling system is in a first location, to provide a first sampling frequency of the sensor based upon the first location, to determine that the information handling system is in a second location, and to provide a second sampling frequency of the sensor based upon the second location, wherein the first sampling frequency is different from the second sampling frequency; and
   a database including a plurality of entries, each entry including a historical location and historical sensor information for the environmental factor as measured by the sensor at the historical location, and a key performance indicator (KPI) information associated with the associated historical sensor information.

2. The information handling system of claim 1 wherein, in response to determining that the information handling system is in the first location, the processor is further configured to retrieve a first entry associated with the first location from the database, and wherein providing the first sampling frequency of the sensor is further based upon first historical sensor information associated with the first location.

3. The information handling system of claim 2, wherein, in response to determining that the information handling system is in the second location, the processor is further configured to retrieve a second entry associated with the second location from the database, and wherein providing the second sampling frequency of the sensor is further based upon second historical sensor information associated with the second location.

4. The information handling system of claim 2, wherein the processor is further configured to predict that the information handling system will be in a third location, retrieve a third entry associated with the third location from the database, and provide third historical sensor information associated with the third location to a user interface of the information handling system.

5. The information handling system of claim 4, wherein the processor is further configured to provide first KPI information associated with the third historical sensor information to the user interface.

6. The information handling system of claim 1, wherein the processor is further configured to receive a first air quality index (AQI) indication for the environmental factor in a region surrounding the information handling system, to provide a third sampling frequency of the sensor based upon the first AQI indication, to receive a second AQI indication for the environmental factor in the region, and to provide a fourth sampling frequency of the sensor based upon the second location, wherein the first AQI indication is different from the second AQI indication, and wherein the third sampling frequency is different from the fourth sampling frequency.

7. The information handling system of claim 6, wherein the processor is further configured to determine that the first AQI indication is different from the second AQI indication, and to provide an indication that the first AQI indication is different from the second AQI indication to a user interface of the information handling system.

8. The information handling system of claim 1, wherein the processor is further configured to set a threshold for the environmental factor as measured in the ambient environment by the sensor, wherein the threshold is set based upon an AQI indication for the environmental factor in a region surrounding the information handling system.

9. The information handling system of claim 8, wherein the processor is further configured to provide an indication to a user interface of the information handling system when the sensor detects that the environmental factor in the ambient environment exceeds the threshold.

10. A method, comprising:
measuring, by a sensor of an information handling system, an environmental factor in an ambient environment immediately surrounding the information handling system;
determining that the information handling system is in a first location;
providing a first sampling frequency of the sensor based upon the first location;
determining that the information handling system is in a second location;
providing a second sampling frequency of the sensor based upon the second location, wherein the first sampling frequency is different from the second sampling frequency;
in response to determining that the information handling system is in the first location, retrieving a first entry of a database, the database including a plurality of entries, each entry including a historical location and historical sensor information for the environmental factor as measured by the sensor at the historical location, wherein the first entry is associated with the first location, and wherein each entry further includes a key performance indicator (KPI) information associated with the associated historical sensor information.

11. The method of claim 10 wherein providing the first sampling frequency of the sensor is further based upon first historical sensor information associated with the first location.

12. The method of claim 11, wherein, in response to determining that the information handling system is in the second location, the method further comprises retrieving a second entry associated with the second location from the database, wherein providing the second sampling frequency of the sensor is further based upon second historical sensor information associated with the second location.

13. The method of claim 11, further comprising predicting that the information handling system will be in a third location; retrieving a third entry associated with the third location from the database; and providing third historical sensor information associated with the third location to a user interface of the information handling system.

14. The method of claim 10, further comprising providing first KPI information associated with the third historical sensor information to the user interface.

15. The method of claim 10, further comprising:
receiving a first air quality index (AQI) indication for the environmental factor in a region surrounding the information handling system;
providing a third sampling frequency of the sensor based upon the first AQI indication;
receiving a second AQI indication for the environmental factor in the region; and
providing a fourth sampling frequency of the sensor based upon the second location, wherein the first AQI indication is different from the second AQI indication, and wherein the third sampling frequency is different from the fourth sampling frequency.

16. The method of claim 15, further comprising:
determining that the first AQI indication is different from the second AQI indication; and
providing an indication that the first AQI indication is different from the second AQI indication to a user interface of the information handling system.

17. The method of claim 10, further comprising:
setting a threshold for the environmental factor as measured in the ambient environment by the sensor, wherein the threshold is set based upon an AQI indication for the environmental factor in a region surrounding the information handling system; and
providing an indication to a user interface of the information handling system when the sensor detects that the environmental factor in the ambient environment exceeds the threshold.

18. An information handling system, comprising:
a first sensor configured to measure a first environmental factor in an ambient environment immediately surrounding the information handling system;
a second sensor configured to measure a second environmental factor in the ambient environment;
a processor configured to determine that the information handling system is in a first location, to provide a first sampling frequency of the first sensor and a second sampling frequency of the second sensor based upon the first location, to determine that the information handling system is in a second location, and to provide a third sampling frequency of the first sensor based upon the second location, wherein the first sampling frequency is different from the third sampling frequency; and
a database including a plurality of entries, each entry including a historical location and historical sensor information for the first and second environmental factors as measured by the sensor at the historical location, and a key performance indicator (KPI) information associated with the associated historical sensor information.

* * * * *